US006839586B2

(12) United States Patent
Webb

(10) Patent No.: US 6,839,586 B2
(45) Date of Patent: Jan. 4, 2005

(54) USE OF MULTIPHOTON EXCITATION THROUGH OPTICAL FIBERS FOR FLUORESCENCE SPECTROSCOPY IN CONJUNCTION WITH OPTICAL BIOPSY NEEDLES AND ENDOSCOPES

(75) Inventor: Watt W. Webb, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/429,392

(22) Filed: May 5, 2003

(65) Prior Publication Data

US 2003/0191397 A1 Oct. 9, 2003

Related U.S. Application Data

(63) Continuation of application No. 09/779,918, filed on Feb. 7, 2001, now Pat. No. 6,580,941.
(60) Provisional application No. 60/181,012, filed on Feb. 8, 2000.

(51) Int. Cl.$^7$ .................................................. A61B 6/00
(52) U.S. Cl. ....................................................... 600/478
(58) Field of Search .............................. 600/478, 477, 600/113, 101, 182, 447; 356/432; 250/458.1, 461.1, 483.1, 483.2, 483.4, 492.1, 358.1, 484.2, 484.4, 192.1

(56) References Cited

U.S. PATENT DOCUMENTS

| 4,576,173 A | 3/1986 | Parker et al. |
|---|---|---|
| 4,592,361 A | 6/1986 | Parker et al. |
| 4,895,156 A | 1/1990 | Schulze |
| 5,034,613 A | 7/1991 | Denk et al. |
| 5,115,137 A | 5/1992 | Andersson-Engels et al. |

(List continued on next page.)

FOREIGN PATENT DOCUMENTS

| EP | 0 512 965 A1 | 11/1992 |
|---|---|---|
| EP | 0 920 831 A1 | 6/1999 |

OTHER PUBLICATIONS

Tromberg et al., "Optical Fiber Fluoroprobes for Biological Measurements," *Applied Spectroscopy* 38(1):38–42 (1984) ("Tromberg").
Dinkel et al., "Remote Two–Photon Excited Fluorescence Sensing in a Simulated Fermentation Broth," *Analytica Chimica Acta* 263:131–136 (1992) ("Dinkel").
Williams et al., Mucosal Mast Cell Secretion Processes Imaged Using Three–Photon Microscopy of 5–Hydroxytryptamine Autofluorescence, *Biophysical Journal* 76:1835–1846 (1999) ("Williams I").
Xu et al., "Multiphoton Excitation of Molecular Fluorophores and Nonlinear Laser Microscopy," *Topics in Fluorescence Spectroscopy* 5:471–540 (1997).
Shear et al., "Multiphoton–Excited Visible Emission by Serotonin Solutions," *Photochemistry and Photobiology* 65(6):931–936 (1997).
Xu et al., "Multiphoton Excitation Cross–sections of Molecular Fluorophores," *Bioimaging* 4:198–207 (1996).

(List continued on next page.)

*Primary Examiner*—Mahmoud Gimie
(74) *Attorney, Agent, or Firm*—Nixon Peabody LLP

(57) ABSTRACT

The present invention is directed to a method of applying radiation through an optical fiber for detecting disease within a plant or animal or imaging a particular tissue of a plant or animal. In addition, fluorescence can be detected and localized within a subject by such application of radiation through an optical fiber. The radiation is effective to promote simultaneous multiphoton excitation. The optical fibers are used alone to examine internal regions of tissue, in conjunction with an optical biopsy needle to evaluate subsurface tissue, or with an endoscope to evaluate tissue within body cavities.

52 Claims, 8 Drawing Sheets

U.S. PATENT DOCUMENTS

| | | | |
|---|---|---|---|
| 5,119,815 A | 6/1992 | Chance | |
| 5,127,405 A | 7/1992 | Alcala et al. | |
| 5,197,470 A | 3/1993 | Helfer et al. | |
| 5,311,013 A | 5/1994 | Gutcheck et al. | |
| 5,323,775 A | 6/1994 | Joshi et al. | |
| 5,333,044 A | 7/1994 | Shaffer | |
| 5,341,805 A | 8/1994 | Stavridi et al. | |
| 5,353,790 A | 10/1994 | Jacques et al. | |
| 5,419,323 A | 5/1995 | Kittrell et al. | |
| 5,421,337 A * | 6/1995 | Richards-Kortum et al. | 600/477 |
| 5,579,773 A | 12/1996 | Vo-Dinh et al. | |
| 5,590,660 A | 1/1997 | MacAulay et al. | |
| 5,628,310 A | 5/1997 | Rao et al. | |
| 5,697,373 A | 12/1997 | Richards-Kortum et al. | |
| 5,699,795 A | 12/1997 | Richards-Kortum et al. | |
| 5,827,190 A | 10/1998 | Palcic et al. | |
| 5,986,271 A | 11/1999 | Lazarev et al. | |
| 6,070,096 A | 5/2000 | Hayashi | |
| 6,178,041 B1 | 1/2001 | Simon | |
| 6,201,989 B1 | 3/2001 | Whitehead et al. | |
| 6,212,425 B1 | 4/2001 | Irion et al. | |
| 6,238,348 B1 | 5/2001 | Crowley et al. | |

OTHER PUBLICATIONS

Maiti et al., "Measuring Serotonin Distribution in Live Cells with Three–Photon Excitation," *Science* 275:530–532 (1997).

Xu et al., "Multiphoton Fluorescence Excitation: New Spectral Windows for Biological Nonlinear Microscopy," *Proc. Natl. Acad. Sci. USA* 93:10763–10768 (1996).

Lago et al., "Two–Photon–Induced Fluorescence of Biological Markers Based on Optical Fibers," *Optics Letters* 20(20):2054–2056 (1995).

Williams et al., "Two–Photon Molecular Excitation Provides Intrinsic 3–Dimensional Resolution for Laser–based Microscopy and Microphotochemistry," *FASEB Journal* 8:804–813 (1994).

Denk et al., "Two–Photon Molecular Excitation in Laser-Scanning Microscopy," *In Handbook of Biological Confocal Microscopy*, pp. 445–458 (1995).

Webb, "Non–Linear Laser Microscopy," *Progress in Biophysics & Molecular Biology* XIIth International Biophysics Congress, 65:20 (1996) (Abstract).

Webb et al., "Multiphoton Fluorescence Correlation Spectroscopy with Single Molecules in Living Cells," 4$^{th}$ International Weber Symposium on Innovative Fluorescence Methodologies in Biochemistry and Medicine (1999) (Abstract).

Nichols et al., "Visualization of Mitochondria Via Two–Photon Microscopy of NADH: Indentifying Conditions that Maintain Cell Viability," *Biophysics Journal* 76:A9 (1999) (Abstract).

Nichols et al., "Identification of the Principle Sources of Two–Photon Autofluorescence From HeLa Cell Monolayers," *Biophysics Journal* 72:A346 (1997) (Abstract).

Williams et al., "Three–Photon Excitation Imaging of Serotonin Secretion by RBL–2H3 Cells," *Biophysics Journal* 72:A156 (1997) (Abstract).

Xu et al., "Multiphoton Excitation of Molecular Fluorophores and Native Biological Absorbers," *Biophysics Journal* 72:A90 (1997) (Abstract).

Shear et al., "Multiphoton–Excited Photochemistry Yields Visible Emission from Serotonin," (Abstract).

Xu et al., "Multiphoton Excitation of Fluorophores in Nonlinear Laser Microscopy," *OSA ILS–XII/Optics & Imaging in the Information Age* p. 158 (1996) (Abstract).

Webb et al., "Biological Applications of Nonlinear Laser Microscopy," *Advanced Solid–State Lasers,* Twelfth Topical Meeting, p. 65 (1997) (Abstract).

Webb et al., "Multiphoton Molecular Excitation to Illuminate Non–Linear Laser Microscopy," Ultrafast Phenomena, Optical Society of America Technical Digest 8, 170 (1996) (Abstract).

Webb, "Non–Linear Optical Microscopy," *Biophysics Journal* 70:A429 (1996) (Abstract).

Webb, "Non–Linear Laser Microscopy," *Photochemistry and Photobiology* 63:445 (1996) (Abstract).

Xu et al., "Three–Photon Excited Fluorescence and Applications in Nonlinear Laser Scanning Microscopy," *Biophysics Journal* 70:A429 (1996) (Abstract).

Maiti et al., "Multiphoton Fluorescence Spectroscopy Through Optical Fibers," *Biophysics Journal* 72:A217 (1997) (Abstract).

Masters, "Confocal Microscopy and Multi–Photon Excitation Microscopy of Human Skin In Vivo," *Optics Express* 8(1):2–10 (2001).

Masters et al., "Multiphoton Excitation Microscopy of Human Skin In Vivo: Early Development of an Optical Biopsy," *In SFM99* (Saratov Fall Meeting 99), Saratov State University Optics Department, Russia (1999).

Helmchen et al., "A Miniaturized Two–Photon Fiber–Scanning Microscope for In Vivo Imaging," *Society for Neuroscience* vol. 25 (1999) (abstract).

Glanzmann et al., "Time–Resolved Spectrofluorometer for Clinical Tissue Characterization During Endoscopy," *Review of Scientific Instruments* 70(10):4067–4077 (1999).

Arendt et al., "Investigation of Early Cancerous Changes in Bladder Tissue by Autofluorescence," Proceedings—19$^{th}$ International Conference—*IEEE/EMBS* pp. 2290–2293 (1997).

Zonios et al., "Morphological Model of Human Colon Tissue Fluorescence," *IEEE Transactions on Biomedical Engineering* 43(2):113–122 (1996).

* cited by examiner

USE OF MULTIPHOTON EXCITATION THROUGH OPTICAL FIBERS FOR FLUORESCENCE SPECTROSCOPY IN CONJUNCTION WITH OPTICAL BIOPSY NEEDLES AND ENDOSCOPES

This application is a continuation of U.S. patent application Ser. No. 09/779,918, filed Feb. 7, 2001, now U.S. Pat. No. 6,580,941 which claims benefit o U.S Provisional Patent Application Ser. No. 60/181,012, filed on Feb. 8, 2000.

This invention was developed with government funding under National Science Foundation Grant No. BIR 8800278 and National Institutes of Health Grant No. RR04224. The U.S. Government may have certain rights in this invention.

FIELD OF THE INVENTION

The present invention relates to the use of multiphoton excitation in conjunction with optical biopsy needles and endoscopes.

BACKGROUND OF THE INVENTION

Many crucial biological functions are mediated or accomplished by biomolecules and tissue structures that are intrinsically fluorescent. As a result, there is an opportunity to diagnose and study important biological events by measuring and localizing the spectra and tissue fluorescence emission. To investigate in vivo internal processes and structures in large organisms, such as human beings and agricultural animals, endoscopic procedures which penetrates body cavities or even solid tissue may be required.

Endoscopy video imaging in body cavities ordinarily utilizes back-scattered white light applied through the endoscope to form a low-resolution color image of the internal surfaces of these cavities. Physicians often use the changes in shapes and changes in local apparent color (which are often due to changes in blood distribution) to recognize disease states, such as malignant tumors or inflammation. Unfortunately, these clues are frequently not sufficient, especially for detection of the early onset of disease. Diagnostic improvements have been made by quantitative measurements of the light scattering and of tissue fluorescence emission.

Ordinarily, the light required to excite the fluorescence of tissue is delivered through an optical fiber or fiber bundle that is inserted through a small tube built into the endoscopic pipe to accommodate a mechanical biopsy wire. Small optical fibers or fiber bundles can be passed easily through the same tube. Some of the strongest tissue fluorescence usually seen in this procedure are due to NADH (nicotinamide adenine dinucleotide) and to collagen structures. Their fluorescence is excited by absorption of ultraviolet light of about 300 to 400 nm wavelength corresponding to photon energies of around 3 to 4 eV or sometimes slightly longer wavelength visible light.

A first problem is that this ultraviolet light is strongly absorbed by hemoglobin and oxyhemoglobin in the blood, which are not fluorescent, so that penetration of the illumination into the tissue depends on their concentration and distribution.

A second problem is that the illumination exiting the optical fibers into tissue fans out at an included angle determined by the numerical aperture (NA) of the optical fiber. Small lenses can focus the spread so that the light first converges to a focus but it then fans out beyond the focal plane. (Typically, the NA is about 0.2 and the included cone angle is ~17°.) This angular spreading is a problem, because roughly equal total amounts of fluorescence are excited in every spherical section at each distance from the end of the fiber until attenuated by absorption. This effect is schematically illustrated in FIG. 1. Fluorescence excitation is similarly spread out. Scattering does not attenuate the fluorescence excitation but does distribute it even more broadly. Consequently, the volume observed is ill defined with its practical limits depending also on blood distribution and light scattering. It should be noted that these problems tend to persist even if lenses focus the illumination and/or prisms and mirrors deflect the light for side viewing.

The present invention is directed to overcoming these deficiencies in the art.

SUMMARY OF THE INVENTION

One aspect of the present invention relates to a method of detecting disease within a particular tissue of a plant or animal. This method involves activating the particular plant or animal tissue by application of radiation through at least one optical fiber under conditions effective to promote a simultaneous multiphoton excitation of the particular plant or animal tissue and to emit an intrinsic fluorescence characteristic. The intrinsic fluorescence characteristic is compared to fluorescence emitted by exciting healthy tissue of the particular plant or animal under the same conditions used to carry out the activating step. The particular tissue of a plant or animal where the intrinsic fluorescence characteristic differs from the fluorescence, emitted by exciting healthy tissue of the particular plant or animal under the same conditions used to carry out such activity, is then identified as potentially diseased.

Another aspect of the present invention involves a method of producing an image of an internal surface of a particular tissue within a plant or animal. In this method, the particular plant or animal tissue is activated with radiation applied through an optical fiber under conditions effective to promote a simultaneous multiphoton excitation of the internal surface of the particular tissue within the plant or animal and produce an autofluorescence. The autofluorescence is collected to produce an image of the internal surface.

The present invention also relates to a method of detecting and localizing fluorescence within a subject by applying radiation to an internal region of the subject through at least one optical fiber. Each fiber terminates in a tip proximate to the internal region. Radiation is applied under conditions effective to cause simultaneous multiphoton absorption of fluorophore molecules within the internal region and, as a result, fluorescent excitation proximate to the tip of the at least one optical fiber.

Another embodiment of the present invention relates to a method of detecting and localizing fluorescence within a body of penetrable material by applying radiation to an internal region of the body of penetrable material through at least one optical fiber. Each fiber terminates in a tip proximate to the internal region. Radiation is applied under conditions effective to cause simultaneous multiphoton absorption of fluorophore molecules within the internal region and, as a result, fluorescent excitation proximate to the tip of the at least one optical fiber.

The present invention utilizes multiphoton absorption to excite autofluorescence of tissue with good spatial resolution in order to recognize disease by autofluorescence spectroscopy. The most useful tissue fluorescence for this purpose is most likely to require absorption of ultraviolet energies for excitation. Multiphoton excitation provides the added convenience of infrared illumination to provide the necessary excitation energy by simultaneous absorption of two or more photons by the fluorescent molecules or structures.

The same advantages described above for internal multiphoton excitation of fluorescence spectroscopy through optical fibers penetrating a body cavity or tissue can be advantageously applied to probe other penetrable materials that are, or can be made, fluorescent. Some examples are: food products, polymeric structures or porous media.

One important advantage of multiphoton excitation is that the illumination is not absorbed by hemoglobin and myoglobin and, in fact, not strongly absorbed by any other common tissue components. Scattering of infrared light by tissue is also significantly less than scattering by ultraviolet wavelengths. The principal advantage of multiphoton excitation, however, for endoscopic fluorescence spectroscopy is that the effective focal volume within which fluorescence is strongly excited is well defined and highly localized (FIG. 2). The reason for this is that the rate of two-photon excitation of fluorescence is proportional to the square of the illumination intensity. For higher multiphoton processes, the power law exponent of the intensity is larger, cubic for three-photon excitation for example. In multiphoton laser scanning microscopy, this higher power law feature makes possible three-dimensional resolution without generating out-of-focus fluorescence that would have to be excluded by confocal spatial filtering.

Nearly the same illumination conditions are also suitable for generation of second and third harmonic generation in certain suitable tissues. The second and third harmonics are generated, respectively, at exactly one half and one third of the laser illumination wavelengths and can be used with the intrinsic fluorescence to help characterize the tissue.

An analogous advantage applies to fluorescence multiphoton excited by laser light transmitted through an optical fiber as in application to endoscopic tissue fluorescence. Although the illumination intensity fans out just as for one-photon excitation with roughly equal total power at each value of radius from the end of the fiber or focal plane of any focusing lens, the excited fluorescence does not follow this fanned out illumination. In the case of two-photon excitation through a single mode optical fiber, the distribution of fluorescence is localized near the fiber tip in a shape resembling a candle flame beginning at the fiber tip. This effective focal volume is defined by the spatial distribution of the square of the illumination intensity for two-photon excitation. The square of the illumination intensity falls off roughly as the reciprocal fourth power of the distance from the fiber tip so that the fluorescence excitation is localized. Significant fluorescence is emitted only from this limited volume where the square of the excitation intensity is large, as illustrated in FIG. 3. Lenses, prisms, etc. can be used to shift the effective focal volume beyond the end of the optical fiber and/or to provide a side-looking orientation without losing the advantages of multiphoton excitation.

This effect provides a well-defined focal volume for the fluorescence excitation and allows useful spatial resolution which is sharp enough to resolve important anatomical structures. For example, in the colon, about 5 distinct layers should be distinguishable. At the surface of the endothelium, an array of crypts covers the area and is terminated in a cellular layer that closes the bottoms of the crypts, followed by several more layers including smooth muscle and connective tissue for a total of about 0.5 mm. These layers are readily resolved by multiphoton laser scanning microscopy exciting the intrinsic tissue fluorescence, which differs from layer to layer. Such layers and their perturbations by disease near the surface are thus distinguishable in the intact tissue by endoscopic spectroscopy of the tissue fluorescence with sufficient spatial resolution as provided by multiphoton excitation.

The multiphoton excitation of the present invention allows accurate spatial discrimination and permits quantification of fluorescence from small volumes whose locations are defined in three dimensions. This is especially important in cases where thicker layers of cells are to be studied. In this case, the fiber can penetrate the tissue to observe and resolve the multiphoton excited fluorescence of deeper layers, thus providing optical biopsy in situ. Furthermore, multiphoton excitation greatly reduces the background fluorescence and scattering artifacts.

DETAILED DESCRIPTION OF THE INVENTION

Figure 1:
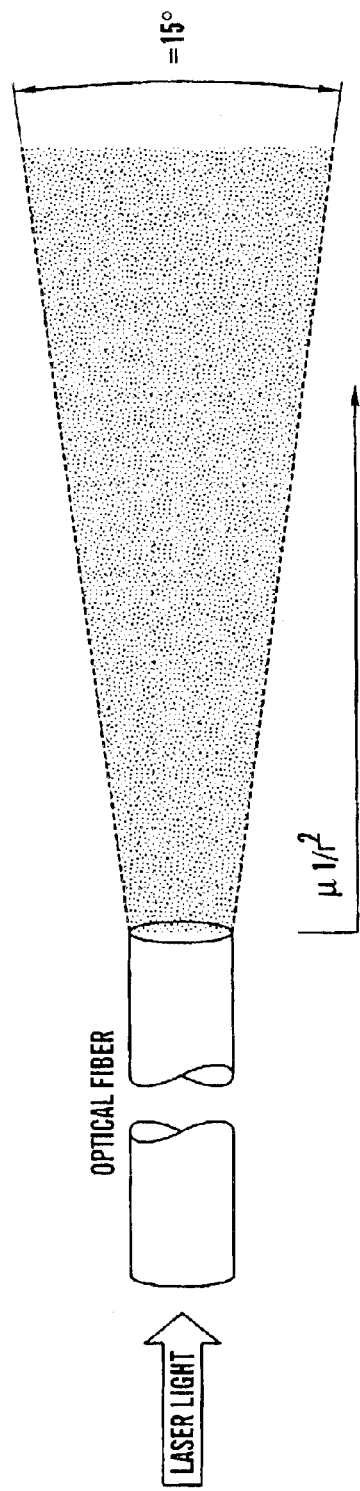
FIG. 1 is a perspective drawing showing the spatial distribution of ultraviolet light emitted from a single mode optical fiber as well as the corresponding autofluorescence in accordance with the prior art. Here, the drop in intensity of radiation is reciprocal to the square of the distance from the tip of the optical fiber.

One aspect of the present invention relates to a method of detecting disease within a particular tissue of a plant or animal. This method involves activating the particular plant or animal tissue by application of radiation through at least one optical fiber under conditions effective to promote a simultaneous multiphoton excitation of the particular plant or animal tissue and to emit an intrinsic fluorescence characteristic. The intrinsic fluorescence characteristic is compared to fluorescence emitted by exciting healthy tissue of the particular plant or animal under the same conditions used to carry out the activating step. The particular tissue of a plant or animal where the intrinsic fluorescence characteristic differs from the fluorescence, emitted by exciting healthy tissue of the particular plant or animal under the same conditions used to carry out such activity, is then identified as potentially diseased.

Another aspect of the present invention involves a method of producing an image of an internal surface of a particular tissue within a plant or animal. In this method, the particular plant or animal tissue is activated with radiation applied through an optical fiber under conditions effective to promote a simultaneous multiphoton excitation of the internal surface of the particular tissue within the plant or animal and produce an autofluorescence. The autofluorescence is collected to produce an image of the tissue under the internal surface by recording a set of adjacent volumes.

The present invention also relates to a method of detecting and localizing fluorescence within a subject by applying radiation to an internal region of the subject through at least one optical fiber. Each fiber terminates in a tip proximate to the internal region. Radiation is applied under conditions effective to cause simultaneous multiphoton absorption of fluorophore molecules within the internal region and, as a result, fluorescent excitation is proximate to the tip of the at least one optical fiber.

Another embodiment of the present invention relates to a method of detecting and localizing fluorescence within a body of penetrable material by applying radiation to an internal region of the body of penetrable material through at least one optical fiber. Each fiber terminates in a tip proximate to the internal region. Radiation is applied under conditions effective to cause simultaneous multiphoton absorption of fluorophore molecules within the internal region and, as a result, fluorescent excitation proximate to the tip of the at least one optical fiber.

One form of the present invention involves the use of multiphoton endoscopic autofluorescence spectroscopy of tissue surfaces inside the cavities of living organisms. Endoscopic inspection and imaging at low resolution of the internal surfaces of body cavities is already a well-established standard medical procedure. Multiphoton endoscopic autofluorescence spectroscopy through optical fibers allows resolution of surface autofluorescence separately from the autofluorescence of underlying layers of the tissue. There are potentially numerous future improvements. Already it is possible to steer, point, and focus optical fibers with control apparatus to detect the fluorescence of tissue regions of interest in the endoscopy of body cavities. Analogous techniques are applicable to achieve the advantages of multiphoton fluorescent excitation for endoscopy. It can be anticipated that scanning of fibers or successive illumination of individual fibers or clusters in a bundle can be used to form multiphoton intrinsic fluorescence images. This aspect of the present invention can be used to image the fluorescence of tissues in internal channels such as the colon, esophagus, stomach, intestine, bladder, uterus, vagina, lung, ovaries, and throat. As a result, malignancy can be detected by recognition of differences in the fluorescence excited with ultraviolet excitation energies.

Figure 2:
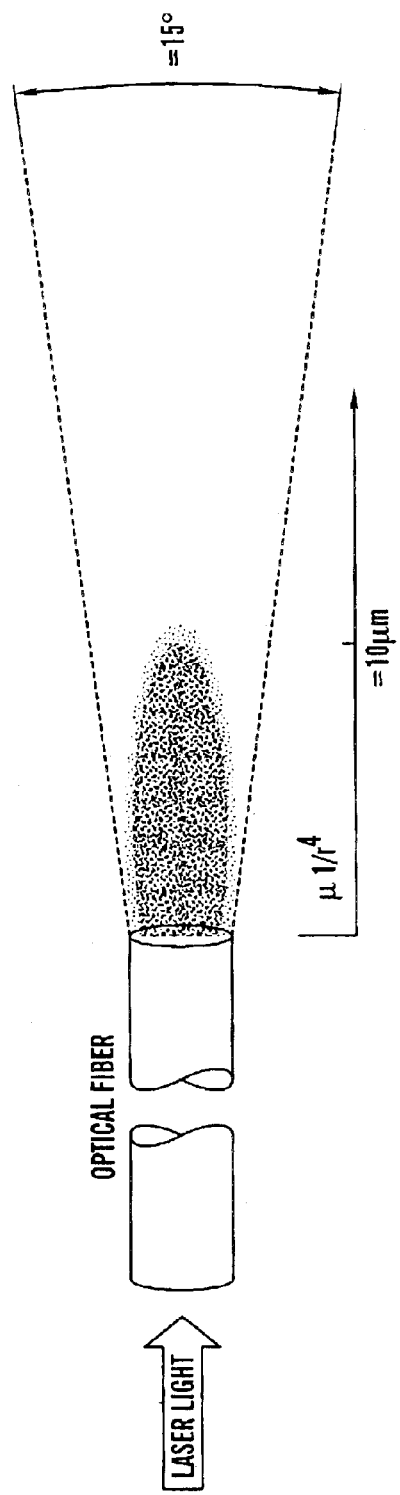
FIG. 2 is a perspective drawing showing the spatial distribution of ultraviolet light of two photon excitation fluorescence emitted from a single mode optical fiber in accordance with the present invention. Here, the pattern of illumination is nearly the same as for one-photon excitation. However, because the rate of two photon excitation is proportional to the square of the pulsed illumination intensity, the fluorescence intensity decreases from the tip of the fiber approximately as the reciprocal fourth power of the distance from the tip of the fiber providing a highly localized effective focal volume for excitation of the fluorescence. For higher order fluorescence excitation, the power law concentration of the emission is even stronger, reciprocal six power for three-photon excitation for example, although the sharpness of the effective focal volume could be reduced if a larger diameter optical fiber is used.
Figure 3:
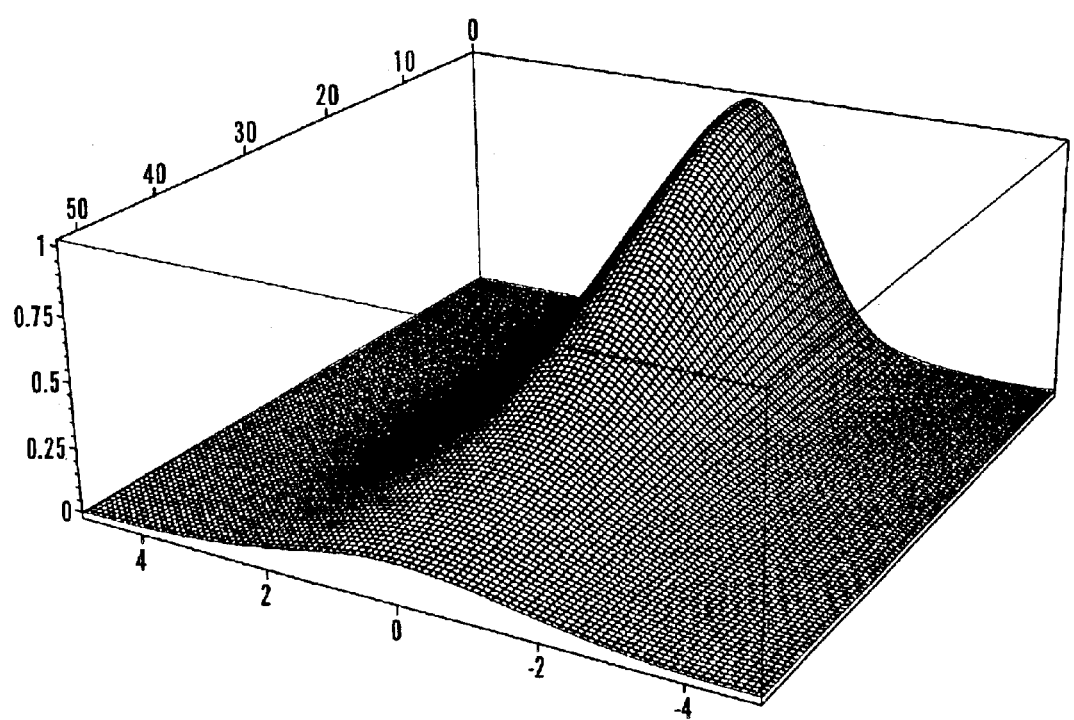
FIG. 3 shows a two photon excitation profile at the fiber output in the form of a Gaussian Intensity Profile. This figure is a representation of the spatial distribution of the two-photon excited fluorescence emission from a uniform fluorophore shown for a plane along the axis of the optical fiber beginning at the exit from the fiber. The normalized maximum drops by half in about 10–15 micrometers along the axis and has a half maximum half-width of about 2 $\mu$m at the exit of this typical single mode fiber.
Figure 4A:
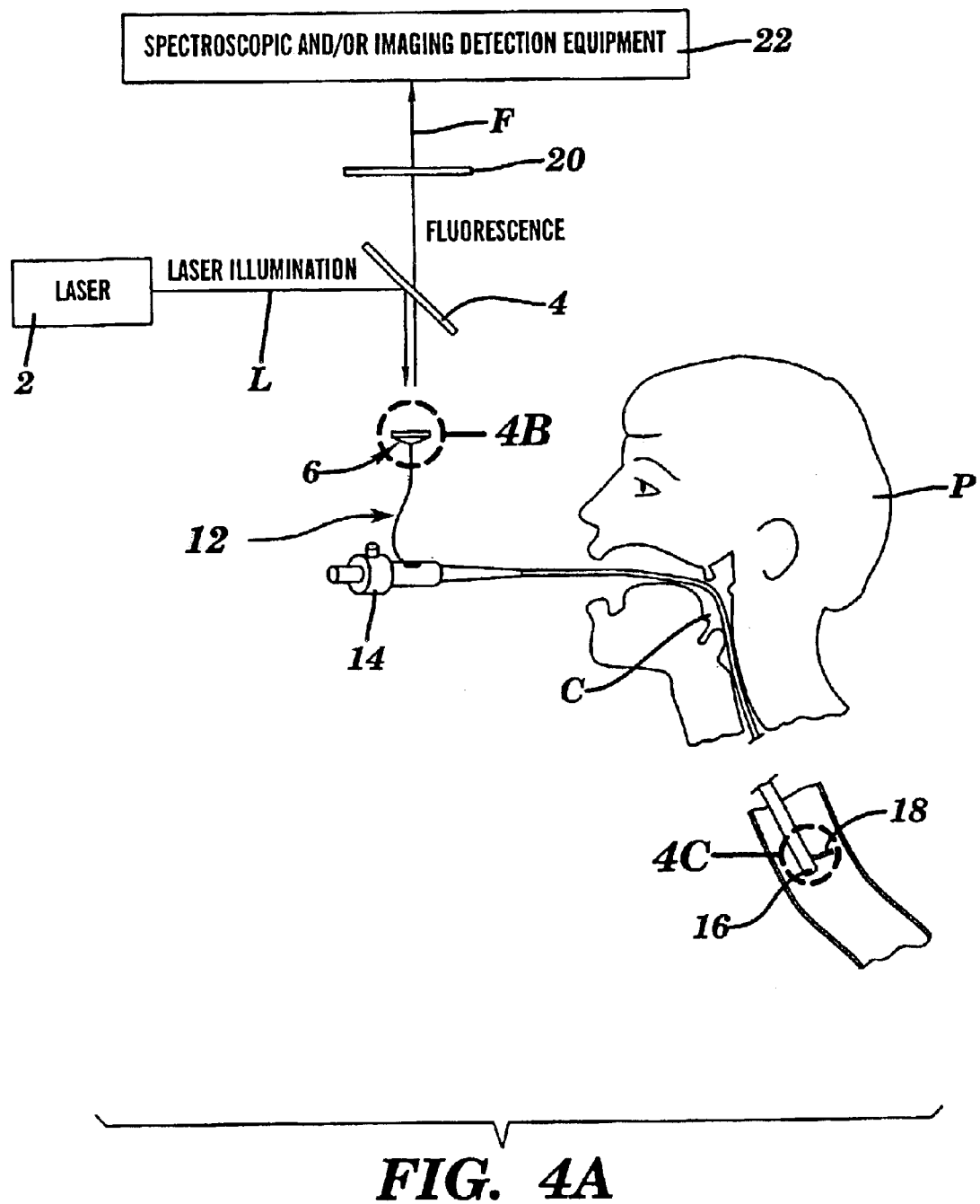
FIGS. 4A–4C show an endoscope arrangement in accordance with the present invention.
Figure 4B:
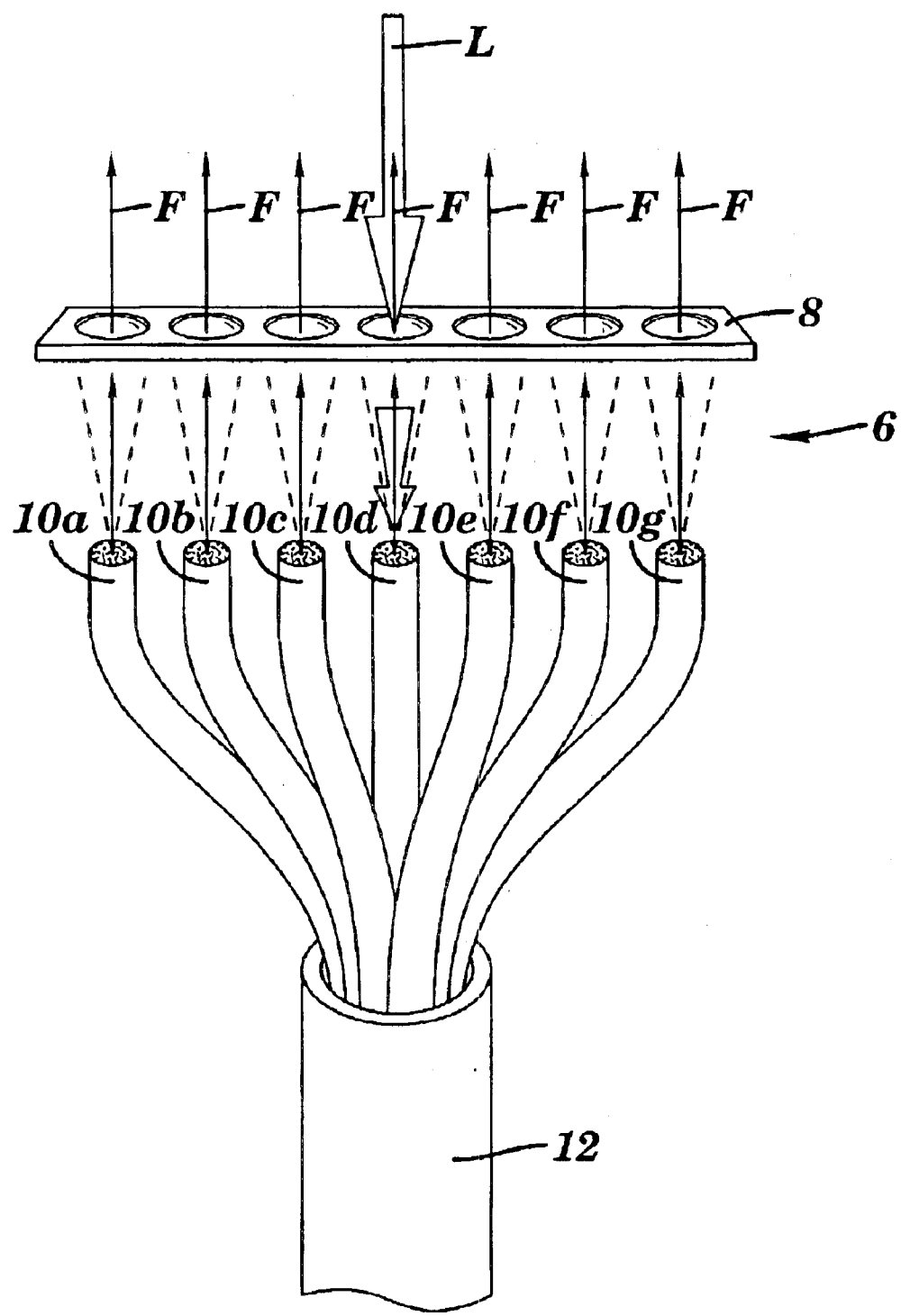
Figure 4C:
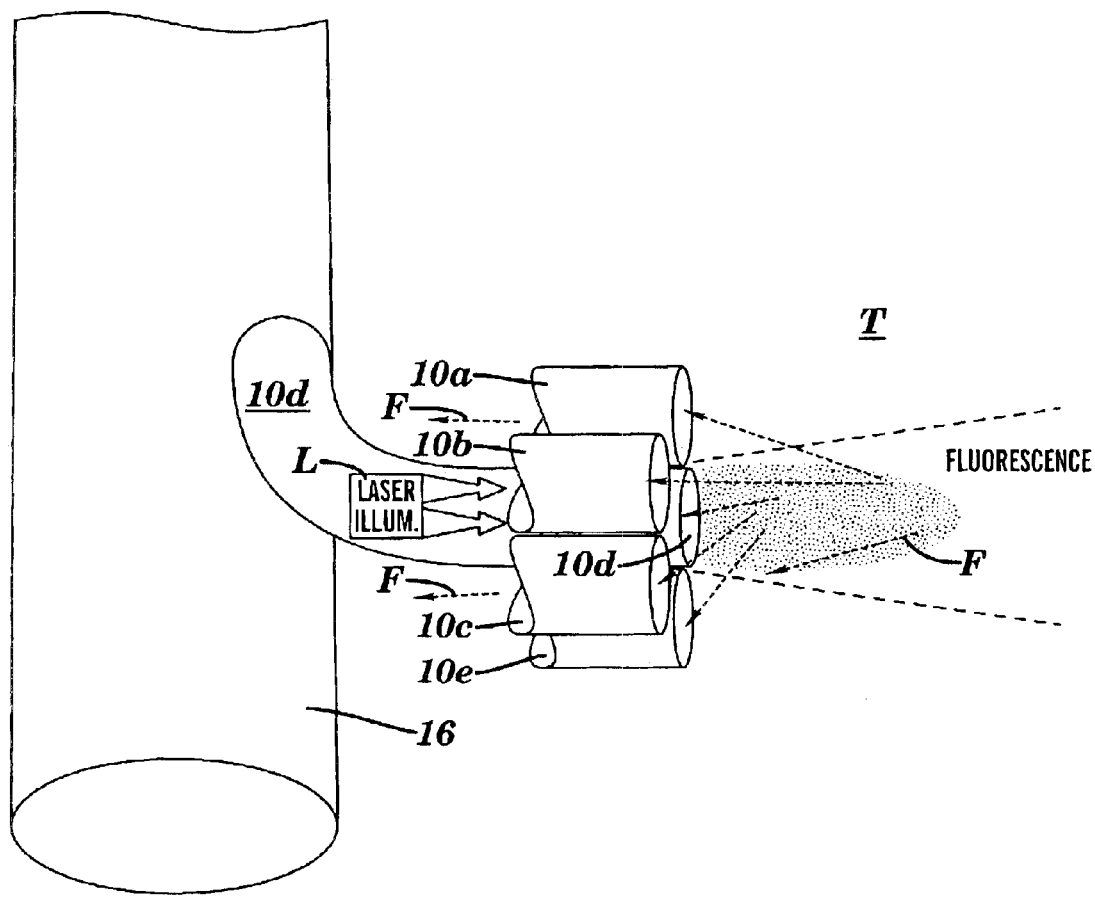

FIGS. 4A–4C show an endoscope arrangement in accordance with the present invention. In this embodiment of the present invention, laser 2 produces laser illumination L which is directed by dichroic filter 4 into optical fiber assembly 6. FIG. 4B shows optical fiber assembly 6 in more detail where laser illumination L passes through lens/focusing array 8 and into optical fiber 10d. Optical fibers 10a–10g are housed in cable 12 which is connected to endoscope head piece 14. The distal end of the endoscope is passed into the mouth of patient P through cavity C which, in this case, is the esophagus. The distal end of the endoscope terminates in endoscope tip 16 and excitation/collection unit 18. As shown in FIG. 4C, which shows excitation/collection unit 18 in more detail, laser illumination L passes through optical fiber 10d and is directed at tissue T. As a result, tissue T fluoresces at the tip of optical fiber 10d (see FIG. 2), and such fluorescence F is collected by optical fibers 10a–10g. The collected fluorescence F passes, in seriatim, through endoscope head piece 14, optical fiber assembly 6 (including lens/focusing array 8), dichroic filter 4, barrier filter 20, and into spectroscopic and/or imaging detection equipment 22.

Another form of the present invention is based on penetration of tissue itself with either at least one conventional optical fiber or with an optical biopsy needle. In this application, the optical fiber or optical biopsy needle is inserted in the tissue itself to sample the autofluorescence of the tissue at the end of the fiber or fibers. The fiber can function like a hypodermic syringe which can be inserted into the tissue as needed. Alternatively, the optical fiber's distal end can be configured to abut the surface of the plant or animal tissue being imaged. With multiphoton excitation, the volume at the end of the fiber where fluorescence is excited is well defined in principle. This can be carried out with a bundle of fibers wrapped around an initial fiber. Alternatively, a bundle of fibers which illuminate a larger volume can be utilized. In biopsy of dense tissue cancers, such as breast or liver cancer, the fiber can probe the fluorescence along insertion pathways. Note that in contrast with conventional biopsy, which generally requires time consuming tissue fixing and staining procedures, the optical biopsy with multiphoton excited fluorescence spectroscopy provides immediate diagnostic spectral data as the probe is inserted and moved within the patient.

Figure 5A:
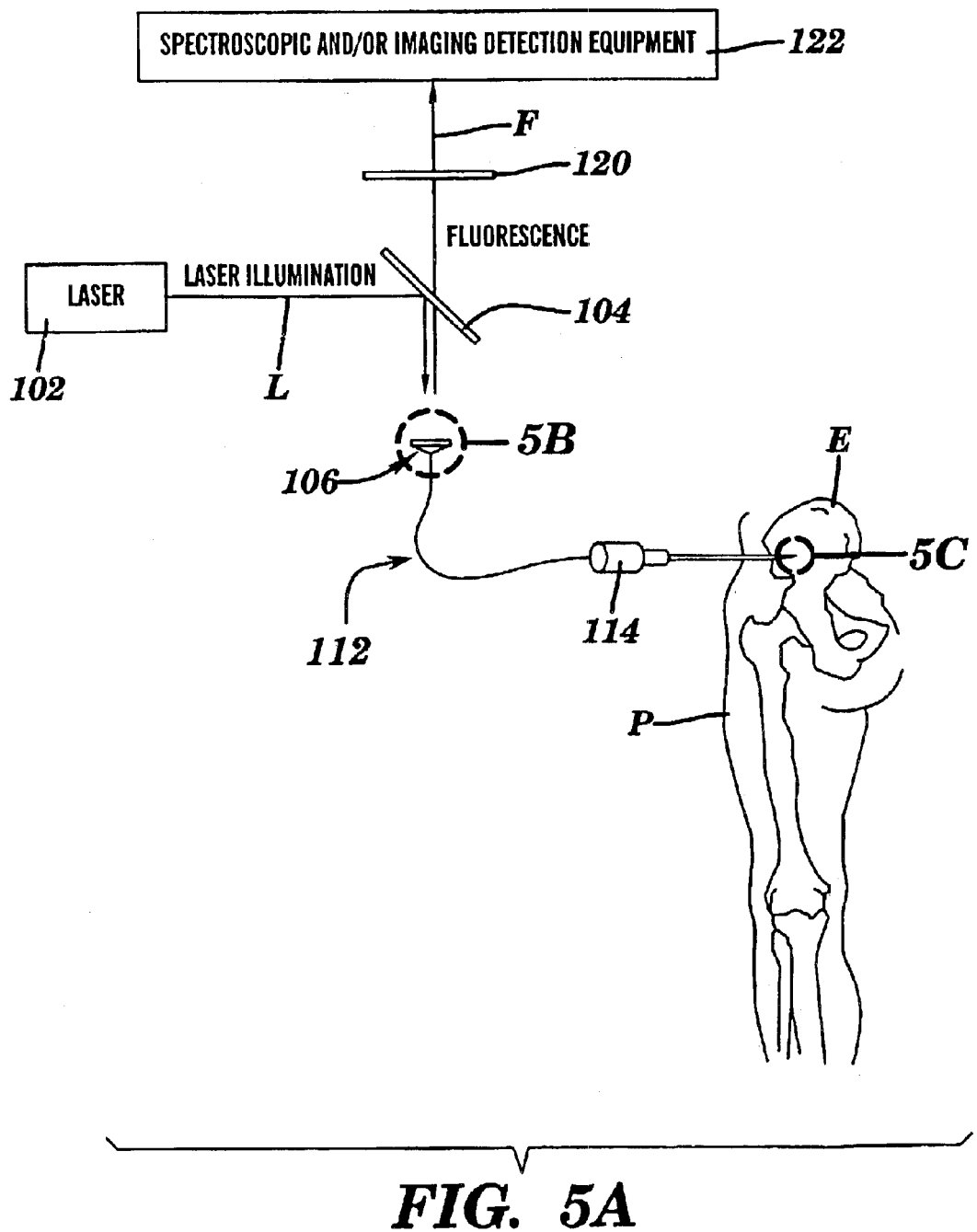
FIGS. 5A–5C show an optical biopsy needle arrangement in accordance with the present invention.
Figure 5B:
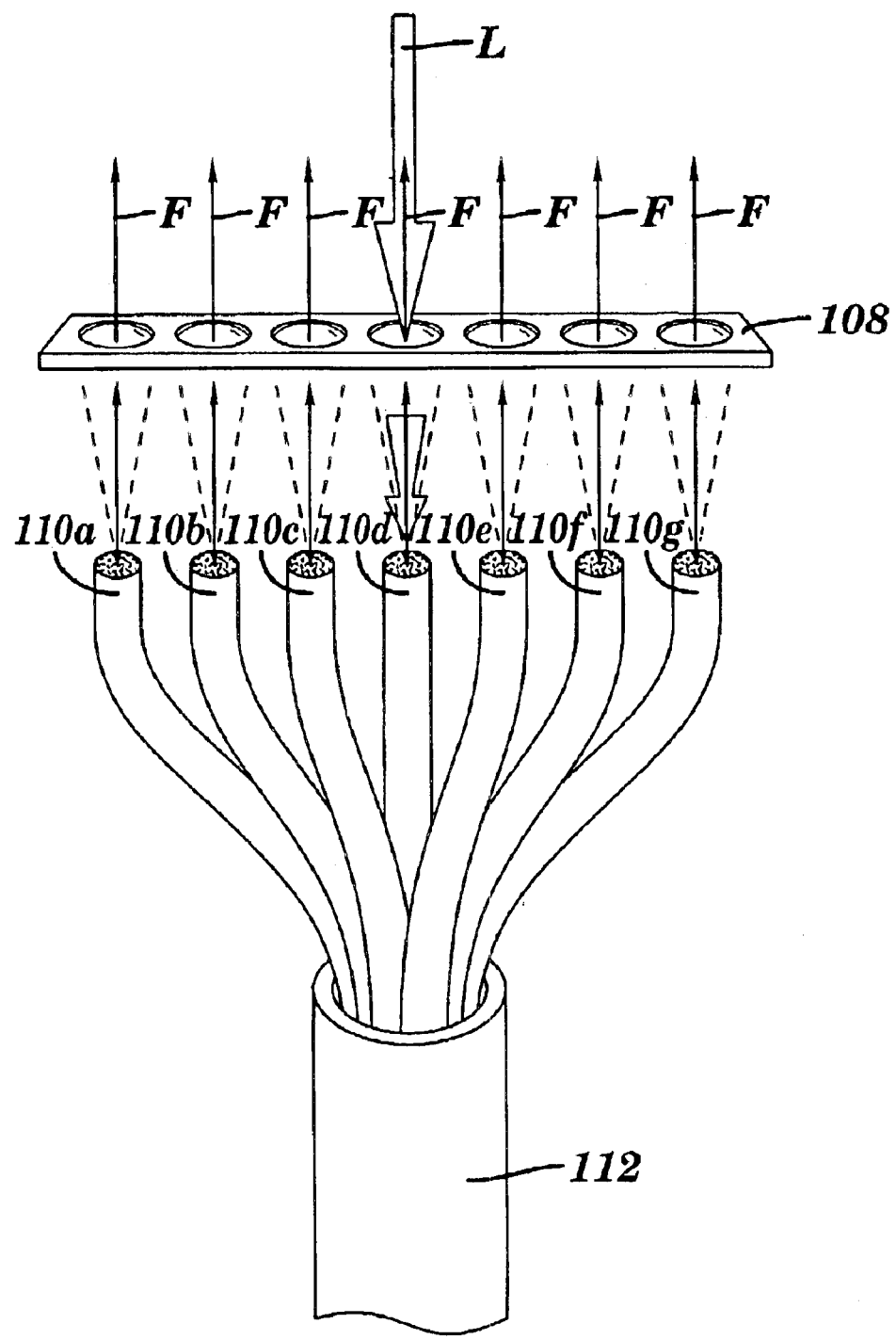
Figure 5C:
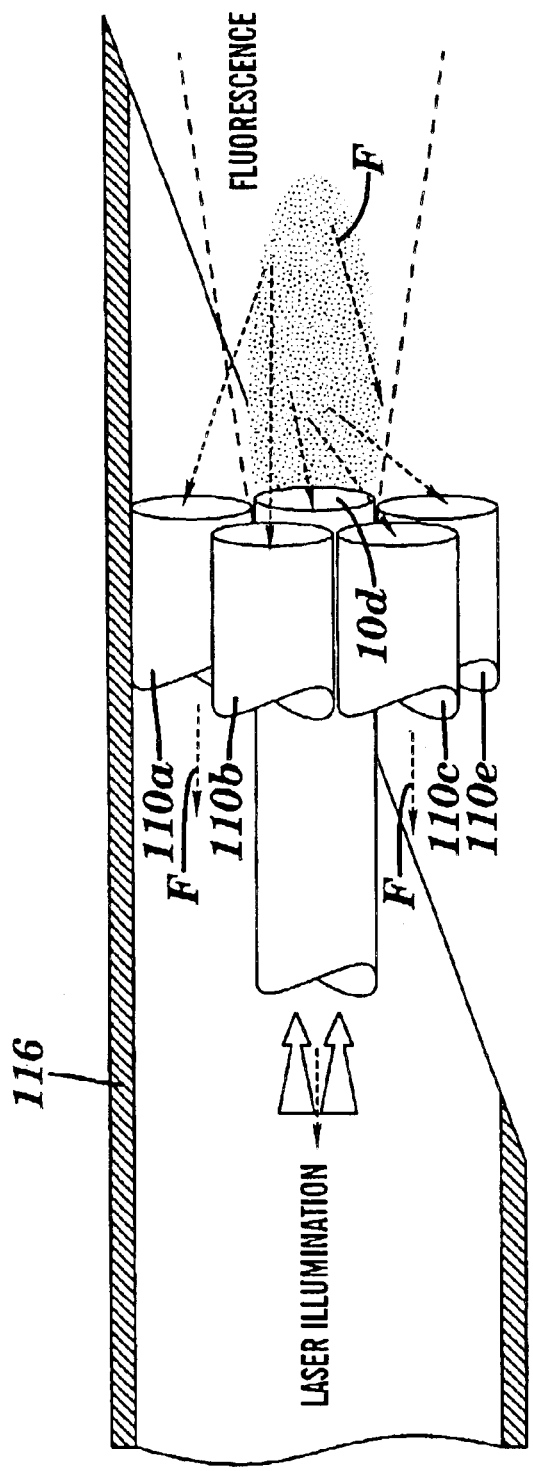

FIGS. 5A–5C show an optical biopsy needle arrangement in accordance with the present invention. In this embodiment of the present invention, laser 102 produces laser illumination L which is directed by dichroic filter 104 into optical fiber assembly 106. FIG. 5B shows optical fiber assembly 106 in more detail where laser illumination L passes through lens/focusing array 108 and into optical fiber 110d. Optical fibers 110a–10g are housed in cable 112 which is connected to optical biopsy needle head piece 114. The distal end of the optical biopsy needle (i.e. needle 116) is passed through the skin of patient P and into pelvis E. As shown in more detail in FIG. 5C, within needle 116, laser illumination L passes through optical fiber 10d and is directed at tissue T. As a result, tissue T fluoresces at the tip of optical fiber 10d (see FIG. 2), and such fluorescence F is collected by optical fibers 110a–110g. The collected fluorescence F passes, in seriatim, through optical biopsy needle head piece 114, optical fiber assembly 106 (including lens/focusing array 108), dichroic filter 104, barrier filter 120, and into spectroscopic and/or imaging detection equipment 122.

These forms of the present invention can also be carried out in combination where an endoscopic is inserted into a body cavity of a patient to provide a route for fibers to reach an internal surface of a body cavity from which the fibers can be inserted into the tissue to sample its successive layers. For example, in the search for the onset of cancer in the wall of the colon, the tissue has about 5 layers, each with its own characteristic optical properties and autofluorescence. Successive optical probing of each layer can distinguish them and recognize their changes by disease.

Detection of the multiphoton excited fluorescence and the second and third harmonic of the laser excitation generated in the tissue can be accomplished by endoscopy and optical biopsy through the optical fiber that provides the excitation and of course through surrounding fibers in a bundle or through thick optical tubes for efficient collection of light excited near the tip of the single mode excitation fiber or fibers. There is a significant advantage in fluorescence collection efficiency for multiphoton endoscopic tissue fluorescence over single photon excitation, because the emission is localized near the fiber tip where it is most accessible to collection optics. The same advantage applies in optical biopsy. Desirably, the present invention is carried out with a plurality of optical fibers, including a single excitation fiber surrounded by a plurality of collection fibers.

Effective multiphoton molecular excitation is made possible, in accordance with the present invention, by the combination of (a) the very high, local, instantaneous intensity and (b) the temporal concentration of a pulsed laser. A high intensity, long wavelength, monochromatic light source which is focusable to the diffraction limit such as a titanium sapphire mode locked solid state laser, with each pulse having a duration of about 100 femtoseconds ($100 \times 10^{-15}$ seconds) at a repetition rate of about 80 MHz. Other lasers that are also effective for multiphoton excitation and harmonic generation can also be used. These fast pulses are directed through the endoscope or optical biopsy needle to target tissue within a living plant or animal or, alternatively, a tissue specimen. Because of the high instantaneous power provided by the very short duration intense pulses focused to the diffraction limit, there is an appreciable probability that a fluorophore (a fluorescent dye), contained in the target, and normally excitable by a single high energy photon having a short wavelength, typically ultraviolet, will absorb two long wavelength photons from the laser source simultaneously. This absorption combines the energy of the two photons in the fluorophore molecule, thereby raising the fluorophore to its excited state. When the fluorophore returns to its normal state, it emits light, and this light then passes back through the endoscope or optical biopsy needle to a suitable detector.

The multiphoton excitation of fluorophores by highly intense, short pulses of light constitutes a general fluorescence microscopy technique for imaging which provides improved background discrimination and reduces photobleaching of the fluorophores. This is because the focused illumination provided in the microscope fills a converging cone as it passes into the specimen. All of the light which reaches the plane of focus at the apex of the converging cone, except the tiny fraction which is absorbed in the fluorophore, then passes out the opposite side of the specimen through a diverging cone. Only in the region of the focal point on the object plane at the waist formed by the converging and diverging cones is the intensity sufficiently high to produce multiphoton absorption in the specimen fluorophore, and this intensity dependence enables long wavelength excitation only in the small local volume of the specimen surrounding the focal point. This absorption is produced by means of a stream of fast, high intensity, femtosecond pulses of relatively long wavelength which retains a moderate average illumination intensity of long wavelength light throughout the remainder of the specimen outside the region of the focal point. As a result, photobleaching of the fluorophore outside the plane of focus is virtually eliminated. One-photon absorption of the long wavelength light is negligible, and outside the plane of focus the instantaneous intensity is too low for appreciable two-photon absorption and excitation, even though the time average illumination is in reality nearly uniform throughout the depth of the specimen. This effect also significantly reduces the damage to living cells.

In order to obtain three dimensional resolution, the present invention can utilize two-photon excitation of a fluorophore which has a one-photon absorption peak at a wavelength which overlaps or exceeds one-half that of the exciting light. For three-photon excitation, the one-photon absorption overlaps one-third that of the exciting light. To accomplish this, the laser produces a very short pulsed laser beam of high instantaneous power and of a relatively long wavelength, for example in the visible red of the infrared range. This light is directed to a specimen containing a fluorophore normally excited by a single photon having a short wavelength (e.g., ultraviolet radiation) range so that two low energy (red) photons must combine their energy to provide the same excitation of the specimen that would be provided by a single high energy (ultraviolet) photon. Both the excitation and hence the fluorescence rates in the specimen are proportional to the square of the intensity of the incident light. In the focused excitation laser beam, the intensity of the long wavelength incident light becomes high enough to excite the fluorophores in the specimen only in the region of the focal point. This focal point may be adjustably positioned within the specimen so that fluorescence and/or photolysis of the specimen are produced only in a selected ellipsoidal volume around the focus. Thus, in accordance with the present invention, only long wavelength excitation light has to pass through the specimen, and this long wavelength light is focused to produce sufficient intensity to excite fluorescence only in a very small region. This fluorescence is produced even if the fluorophore normally absorbs only in the ultraviolet. Since the focal point can be selectively positioned in the specimen, three-dimensional resolution is provided in both scanning fluorescence microscopy and in photolysis, including photolysis of photon-activatable reagents which can be released by photolysis.

In accordance with the present invention, the necessary excitation intensity is provided from a radiation light source which may be, for example, a titanium sapphire mode locked laser generating pulses of light having a wavelength in the red region of the spectrum, for example about 700–1000 nm, or with the pulses having a width of $10^{-9}$ seconds to $10^{-15}$ seconds, conveniently at about 80 MHz repetition rate. Other bright pulsed lasers may also be used to produce light at different relatively long wavelengths in the infrared or visible red region of the spectrum, for example, to generate the necessary excitation photon energies which will add up to the appropriate absorption energy band required by the fluorophores in the spectrum which normally would be excited by absorption of a single photon in the spectral region having wavelengths about one-half the wavelength of the incident light. If shorter excitation wavelengths are needed, the laser wavelengths can be divided by 2, 3, or 4 by external harmonic generation. Thus, for example, two photons in the visible red region at 750 nm would combine to excite a fluorophore which normally absorbs light in the ultraviolet region at or above 375 nm, while two photons in the infrared region of, for example, 1070 nm, would excite a fluorophore which absorbs at or above 535 nm in the visible light region.

In a modified form of the invention, the single wavelength light source can be replaced by two different long wavelength laser sources so that the incident light beam consists of two superimposed pulsed light beams of high instantaneous power and of different wavelengths. The wavelengths of the incident beam are selected to excite a fluorophore which is absorbent at a short wavelength which may be described as:

$$1/\lambda_{abs} = 1/\lambda_1 + 1/\lambda_2$$

where $\lambda_{abs}$ is the short wavelength of the absorber, and $\lambda_1$ and $\lambda_2$ are the laser incident beam wavelengths.

In two-photon excitation, with a typical two-photon cross section δ of:

$$\delta = 10^{-58} m^4 s/\text{photon}$$

with the pulse parameters given above (100 fsec. pulses at a repetition rate of 80 MHz), and with the beam focused by a lens of numerical aperture A-1.4, the average incident laser power ($P_0$) of approximately 50 mW saturates the fluorescence output of a fluorophore at the limit of one absorbed photon per pulse per fluorophore. The number $n_a$ of photons absorbed per fluorophore per pulse depends on the following relationship:

$$n_a \approx \frac{P_0^2 \delta}{\tau f^2} \left[ \frac{A^2}{2hc\lambda} \right]^2$$

where

τ is the pulse duration;

f is the repetition rate;

$P_0$ is the average incident laser power;

δ is the photon absorption cross section;

h is the Planck quantum of action;

c is the speed of light; and

A is the numerical aperture of the focusing lens.

The fluorescence emission could be increased, however, by increasing the pulse repetition frequency up to the inverse fluorescence lifetime, which typically is:

$$\tau_f^{-1} = 10^9 s^{-1}$$

For comparison, one-photon fluorescence saturation occurs at incident powers of about 3 mW.

In addition to measurement of intrinsic tissue fluorescence with multiphoton excitation, it is possible to utilize the fluorescence of drugs to detect their location in tissue. Often, such drugs segregate to particular tissue structures or disease products, such as tumors. Multiphoton excitation can be used to identify them. Many important drugs absorb ultraviolet light to become fluorescent and are, therefore, effectively excited by multiphoton excitation. As a result, all of the advantages of multiphoton excitation of intrinsic tissue fluorescence together with the labeling features provided by the selective segregation or binding of fluorescence drugs are achieved. For example, the principal drug used to treat colitis, 5-amino salicylic acid, can be imaged in all of the layers of living colon tissue explants as the drug is metabolized. It can be located relative to complex tissue structure by imaging tissue autofluorescence due to collagen, nicotinamide adenine dinucleotide (NADH), and other structures. Multiphoton excitation of such drugs can be observed in vivo within tissues by multiphoton endoscopy and/or multiphoton optical biopsy.

Photoactive agents including fluorescent dyes are commonly used in multiphoton microscopy to image properties of cells and tissues. Suitable photoactive agents include dyes which are excited by multiphoton excitation such as, organic molecules whose fluorescence changes when they bind metal ions such as $Ca^{2+}$, $Mg^{2+}$, $Na^+$ or $K^+$ or $H^+$. Dyes which bind to the DNA double helix such as DAPI (4',6-diamidino-2-phenylindoledihydrochloride) are particularly useful. Many such dyes are suitable for application in vivo.

Fluorescence distribution could be probed by multiphoton absorption endoscopic spectroscopy in living animals, including humans, to recognize inflammatory disease such as colitis and to follow the progress of its treatment. The distribution of fluorescent protoporphyrin IX, the metabolic product of aminolevulinic acid, which accumulates in cancer cells, would similarly be useful in cancer detection. NADH fluorescence may be the most promising cancer signal accessible by multiphoton absorption endoscopic spectroscopy, but it must be spatially localized by multiphoton absorption to distinguish it from collagen, which is similarly fluorescent in adjacent tissues. It has been known for many years that certain tissues and tissue components, particularly collagen, an important structural component of tissue that appears in many forms, are very effective at generating the second harmonic of bright coherent illumination. The second harmonic of illumination has exactly half of the wavelength and thus twice the photon energy of the fundamental illumination. Similarly, the third harmonic of illumination has exactly one third of the wavelength and, therefore, three times the photon energy. Generation of second harmonic radiation has, in fact, been demonstrated to be a useful phenomenon for microscopic imaging of cells. Because the illumination conditions required to excite second or third harmonic in complex tissue are nearly the same as for multiphoton fluorescence excitation, it is possible to take advantage of second or third harmonic generation, in tissues such as collagen, to complement multiphoton excitation of intrinsic tissue fluorescence. In complex tissues, the second or third harmonic radiation is frequently radiated through broad angles which makes it detectable along with the multiphoton excited fluorescence. The present invention can be used for a variety of purposes. For example, histological and clinical composition, structure, metabolic state, and vitality in the region of the subject can be determined. Alternatively, functional response to physiological and pharmacological stimuli and disease states can be detected in the region of the subject. Lastly, tissue or drug fluorescence excitation and emission spectra, luminosity, fluorescence lifetime, and temporal fluctuations in the region of the subject can be determined.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of detecting disease within a particular tissue of a plant or animal comprising the steps of:

activating the particular plant or animal tissue by application of radiation through at least one optical fiber under conditions effective to promote a simultaneous multiphoton excitation of the particular plant or animal tissue and to emit an intrinsic fluorescence characteristic, wherein said at least one optical fiber has a distal end provided with a terminal focusing lens;

comparing the intrinsic fluorescence characteristic to fluorescence emitted by exciting healthy tissue of the particular plant or animal under the same conditions used to carry out said activating; and identifying the particular tissue of a plant or animal where the intrinsic fluorescence characteristic differs from the fluorescence, emitted by exciting healthy tissue of the particular plant or animal under the same conditions used to carry out said activating, as potentially diseased.

2. The method according to claim 1, wherein the radiation is applied substantially adjacent to the particular plant or animal tissue.

3. The method according to claim 1, wherein the radiation is applied within the particular plant or animal tissue.

4. The method according to claim 1 further comprising:
treating the particular plant or animal tissue with at least one photo-active agent prior to said activating.

5. The method according to claim 1, wherein the radiation is generated by a laser.

6. The method according to claim 5, wherein the radiation is pulsed.

7. The method according to claim 6, wherein the radiation is pulsed at a pulse width between about $10^{-9}$ second to $10^{-15}$ second.

8. The method according to claim 7, wherein the laser is a mode-locked laser.

9. The method according to claim 1, wherein the distal end of the at least one optical fiber abuts a surface of the plant or animal tissue.

10. The method according to claim 1, wherein the at least one optical fiber is disposed within the plant or animal tissue.

11. The method according to claim 10, wherein the at least one optical fiber constitutes or is associated with an optical biopsy needle.

12. The method according to claim 1, wherein the at least one optical fiber is disposed within a body cavity of the plant or animal.

13. The method according to claim 12, wherein the at least one optical fiber is associated with an endoscope.

14. The method according to claim 12, wherein the body cavity is selected from the group consisting of colon, esophagus, stomach, intestine, bladder, uterus, vagina, lung, ovaries, and throat.

15. The method according to claim 1 further comprising:
collecting radiation applied to the plant or animal tissue using one or more collection optical fibers.

16. A method according to claim 1, wherein the tissue is effective to produce second or third harmonics of illumination.

17. A method of producing an image of an internal region of a particular tissue within a plant or animal comprising the steps of:
activating the particular plant or animal tissue with radiation applied through at least one optical fiber under conditions effective to promote a simultaneous multiphoton excitation of the internal region of the particular tissue within the plant or animal and produce an autofluorescence and
collecting the autofluorescence to produce an image of the internal region,
wherein said at least one optical fiber has a distal end provided with a terminal focusing lens.

18. The method according to claim 17, wherein the at least one optical fiber is juxtaposed with a surface of the plant or animal tissue.

19. The method according to claim 17 further comprising:
treating the particular plant or animal tissue with at least one photo-active agent prior to said activating.

20. The method according to claim 17, wherein the radiation is generated by a laser.

21. The method according to claim 17, wherein the radiation is pulsed.

22. The method according to claim 21, wherein the radiation is pulsed at a pulse width between about $10^{-12}$ second to $10^{-15}$ second.

23. The method according to claim 21, wherein the laser is a mode-locked laser.

24. The method according to claim 17, wherein the at least one optical fiber is disposed within a body cavity of the plant or animal.

25. The method according to claim 17, wherein the at least one optical fiber is associated with an endoscope.

26. The method according to claim 17, wherein the body cavity is selected from the group consisting of colon, esophagus, stomach, intestine, bladder, uterus, vagina, lung, ovaries, and throat.

27. The method according to claim 17, wherein the at least one optical fiber is a bundle of optical fibers.

28. A method according to claim 17, wherein the tissue is effective to produce second and third harmonics of illumination.

29. A method of detecting and localizing fluorescence within a subject comprising the steps of:
applying radiation to an internal surface of the subject through at least one optical fiber, each of which has a distal end provided with a terminal focusing lens which terminates in a tip proximate to the internal surface, under conditions effective to cause simultaneous multiphoton absorption of fluorophore molecules within the internal surface and, as a result, fluorescent excitation proximate to the tip of the at least one optical fiber.

30. A method according to claim 29, wherein the at least one optical fiber is inserted into the subject through an externally accessible body cavity of the subject.

31. A method according to claim 30, wherein the at least one optical fiber is associated with an endoscope.

32. A method according to claim 30, wherein the body cavity is selected from the group consisting of colon, esophagus, stomach, intestine, bladder, uterus, vagina, lung, ovaries, and throat.

33. A method according to claim 29, wherein the at least one optical fiber is inserted into the subject through a penetrable surface of the body.

34. A method according to claim 29 further comprising:
imaging the internal surface of the subject after said subjecting.

35. A method according to claim 29 further comprising:
detecting disease in the internal surface of the subject after said applying.

36. A method according to claim 29 further comprising:
treating the subject with at least one photo-active agent prior to said applying.

37. A method according to claim 29, wherein the radiation is generated with a laser.

38. A method according to claim 29, wherein the radiation is pulsed.

39. A method according to claim 38, wherein the radiation is pulsed at a pulse width between about $10^{-12}$ second to $10^{-15}$ second.

40. A method according to claim 39, wherein the laser is a mode-locked laser.

41. A method according to claim 29 further comprising:
detecting histological and clinical composition, structure, metabolic state, and vitality in the internal surface of the subject after said applying.

42. A method according to claim 29 further comprising:
detecting functional response to physiological and pharmacological stimuli and disease states in the internal surface of the subject after said applying.

43. A method according to claim 29 further comprising:
detecting tissue or drug fluorescence excitation and emission spectra, luminosity, fluorescence lifetime, and temporal fluctuations in the internal surface of the subject after said applying.

44. A method according to claim 29, wherein the tissue is effective to produce second and third harmonics of illumination.

45. A method of detecting and localizing fluorescence within a body of penetrable material comprising the steps of:
applying radiation to an internal region of the body of penetrable material through at least one optical fiber, each of which has a distal end provided with a terminal focusing lens which terminates in a tip proximate to the internal region, under conditions effective to cause simultaneous multiphoton absorption of fluorophore molecules within the internal region and, as a result, fluorescent excitation proximate to the tip of the at least one optical fiber.

46. A method according to claim 45, wherein the at least one optical fiber is inserted into the body of penetrable material.

47. A method according to claim 45 further comprising:
imaging the region of the subject after said subjecting.

48. A method according to claim 45, wherein the radiation is generated with a laser.

49. A method according to claim 45, wherein the radiation is pulsed.

50. A method according to claim 49, wherein the radiation is pulsed at a pulse width between about $10^{-12}$ second to $10^{-15}$ second.

51. A method according to claim 50, wherein the laser is a mode-locked laser.

52. A method according to claim 45, wherein the body of penetrable material is effective to produce second and third harmonics of illumination.

* * * * *

UNITED STATES PATENT AND TRADEMARK OFFICE
CERTIFICATE OF CORRECTION

PATENT NO. : 6,839,586 B2
APPLICATION NO. : 10/429392
DATED : January 4, 2005
INVENTOR(S) : Watt W. Webb It is certified that error appears in the above-identified patent and that said Letters Patent is hereby corrected as shown below:

Col. 1 at lines 11-14, delete "This invention was developed with government funding under National Science Foundation Grant No. BIR 8800278 and National Institutes of Health Grant No. RR04224. The U.S. Government may have certain rights in this invention." and insert --This invention was made with government support under grant BIR 8800278 awarded by National Science Foundation and grant RR04224 awarded by National Institutes of Health. The government has certain rights in the invention-- in its place.

Signed and Sealed this

Seventh Day of April, 2009

JOHN DOLL
*Acting Director of the United States Patent and Trademark Office*